US00PP23090P2

(12) United States Plant Patent
van Heesbeen

(10) Patent No.: US PP23,090 P2
(45) Date of Patent: Sep. 25, 2012

(54) *STOKESIA* PLANT NAMED 'MELS BLUE'

(50) Latin Name: *Stokesia laevis*
Varietal Denomination: MELS BLUE

(75) Inventor: Adrianus van Heesbeen, Galder (NL)

(73) Assignee: Van Heesbeen Cultures B.V., Galder (NL)

( * ) Notice: Subject to any disclaimer, the term of this patent is extended or adjusted under 35 U.S.C. 154(b) by 0 days.

(21) Appl. No.: 13/068,928

(22) Filed: May 23, 2011

(51) Int. Cl.
*A01H 5/00* (2006.01)

(52) U.S. Cl. ..... Plt./484

(58) Field of Classification Search ..... Plt./484
See application file for complete search history.

*Primary Examiner* — Kent L Bell
(74) *Attorney, Agent, or Firm* — Cassandra Bright

(57) ABSTRACT

A new and distinct *Stokesia laevis* named 'MELS BLUE' is disclosed, characterized by a distinctive spherical plant shape, strong plant stems, and good branching. The new cultivar is a *Stokesia* typically suited for ornamental container and landscape use.

1 Drawing Sheet

Latin name of the genus and species: *Stokesia laevis.*
Variety denomination: 'MELS BLUE'.

BACKGROUND OF THE INVENTION

The new cultivar is the result of a chance discovery in a commercial nursery in Galder, the Netherlands. The inventor, Adrianus van Heesbeen, a citizen of the Netherlands, discovered the new variety as a single whole plant, mutation of the parent variety, an unpatented, unnamed variety of *Stokesia laevis*. The discovery was made in July of 2007.

After selecting and isolating the new cultivar, asexual reproduction of the new cultivar 'MELS BLUE' was first performed in the same commercial nursery by vegetative division in March 2008. 'MELS BLUE' has since produced multiple generations and has shown that the unique features of this cultivar are stable and reproduced true to type.

SUMMARY OF THE INVENTION

The cultivar 'MELS BLUE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MELS BLUE.' These characteristics in combination distinguish 'MELS BLUE' as a new and distinct *Stokesia* cultivar:

1. Spherical plant shape.
2. Strong plant stems.
3. Higher quantity of plant stems compared to other *Stokesia laevis* varieties.

PARENTAL COMPARISON

Plants of the new cultivar 'MELS BLUE' are similar to the parent, an unpatented, unnamed variety of *Stokesia laevis* in most horticultural characteristics. However, 'MELS BLUE' differs in having a more round overall plant shape. Additionally, the new variety produces plants that have stronger stems and have more stems than the parent variety.

COMMERCIAL COMPARISON

Plants of the new cultivar 'MELS BLUE' are similar to the commercial variety *Stokesia laevis* 'Purple Parasols' U.S. Plant Pat. No. 10,660 in most horticultural characteristics. 'MELS BLUE' differs from 'Purple Parasols' in overall plant form, having a more even, round plant shape. Plants of 'MELS BLUE' have a smaller flower than 'Purple Parasols' and more stems, and stronger plant stems than 'Purple Parasols'.

BRIEF DESCRIPTION OF THE PHOTOGRAPH

The accompanying photograph in FIG. 1 illustrates in full color a typical plant of 'MELS BLUE' grown outdoors in Meer, Belgium. This plant is approximately 12 to 18 months old, grown in a 1 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'MELS BLUE' plants grown outdoors in Meer, Belgium. Measurements were taken in April, before flowering begins. The growing temperature ranged from 0° C. to 25° C. at night to 0° C. to 30° C. during the day. No artificial light, photoperiodic treatments or chemical treatments were given to the plants. Measurements and numerical values represent averages of typical flowering types.

Botanical classification: *Stokesia laevis* 'MELS BLUE'.
Age of the plant described: Approximately 9 months.

Container size of the plant described: 1 liter commercial container.

PROPAGATION

Typical method: Plant division.
Time to rooting: 14 days at 15° C. or higher.
Time to produce a rooted plantlet: 4-5 weeks.
Root description: Well branched, colored near RHS Yellow-white 158C and 158D.

PLANT

Growth habit: Hardy, upright, herbaceous perennial.
Height: Approximately 50 cm.
Blooming period: Naturally blooming in Summer to late Summer.
Plant spread: Approximately 50 cm.
Growth rate: Moderate.
Branching characteristics: Freely branching from base.
Length of lateral branches: Approximately 40 cm.

FOLIAGE

Leaf:
*Arrangement*.—Alternate, simple.
*Average length*.—Approximately 9.6 cm.
*Average width*.—Approximately 3.7 cm.
*Shape of blade*.—Narrow ovate to elliptic.
*Apex*.—Acuminate.
*Base*.—Acuminate.
*Attachment*.—Basal leaves stalked.
*Margin*.—Entire.
*Texture of top surface*.—Smooth, slightly glossy.
*Texture of bottom surface*.—Smooth, slightly glossy.
*Color*.—Young foliage upper side: Near RHS Green 143A, lighter towards the base; 143B and 143C. Young foliage under side: In between near RHS Green 143C and Yellow-Green 144A. Mature foliage upper side: Near RHS Green 137A. Mature foliage under side: Near RHS Yellow-Green 147B.
*Venation*.—Type: Pinnate. Venation color upper side: Near RHS Yellow-Green 145C. Venation color under side: Near RHS Yellow-Green 145B.
Petiole: Basal leaves only.
*Length*.—Approximately 5.0 cm.
*Diameter*.—Approximately 0.4 cm.
*Texture*.—Smooth, moderately glossy.
*Color*.—Near RHS Green 143C.

FLOWER

Bloom period:
*Naturally blooming*.—July-September.
Bud:
*Bud shape*.—Flattened globular.
*Bud length*.—Approximately 1.4 cm.
*Bud diameter*.—Approximately 1.4 cm.
*Bud color*.—Near RHS Yellow-Green 145C with involucral bracts colored Green 143B, top near Purple 76B.
Inflorescence:
*Form*.—Capitula (typical for *Stokesia laevis*).
*Quantity per plant*.—Approximately 130.
Inflorescence:
*Diameter of entire inflorescence*.—Approximately 9.0 cm.
*Depth of inflorescence*.—Approximately 3.6 cm.
*Disc diameter*.—Approximately 5.1 cm.
*Receptacle shape*.—Broad inverted triangular.
*Receptacle height*.—Average 0.4 cm.
*Receptacle diameter*.—Average 0.9 cm.
*Longevity of individual inflorescence*.—Approximately ten days.
*Rate of opening*.—14 to 28 days from bud to fully opened inflorescence.
*Persistent or self-cleaning*.—Self-cleaning.
Ray florets:
*Arrangement*.—Rotate.
*Aspect/orientation*.—Outward.
*Shape*.—Obcordate.
*Number of ray florets*.—Average: 26.
*Length*.—Approximately 4.2 cm.
*Width*.—Approximately 1.7 cm.
*Apex shape*.—Laciniate.
*Base*.—Cuneate.
*Margin*.—Entire.
*Texture*.—Smooth, slightly glossy, slightly velvety.
Color:
*Ray florets*.—Upper surface at first opening: Near RHS Violet-Blue 90C. Upper surface at maturity: Near RHS Violet N88B to 90C. Upper surface at fading: Near RHS Violet N88C. Under surface at first opening: Near RHS Violet-Blue 90D. Under surface at maturity: Near RHS Violet-Blue 90C. Under surface at fading: Near RHS Violet N88C.
Disc/inner ray florets:
*Number of disc florets*.—Approximately 150.
*Arrangement*.—Spirally placed on disc.
*Length*.—Approximately 2.3 cm.
*Width*.—Approximately 0.9 cm.
*Shape*.—Tubular, with an average of 5 free tips, lower 50% fused.
*Margin*.—Margins of free tips entire.
*Apex*.—Acute.
*Base*.—Fused into a tube.
*Texture*.—Smooth, slightly glossy, slightly velvety.
Color:
*Disc florets*.—Upper surface at first opening: Near RHS Violet N88B. Upper surface at maturity: Near RHS Violet N88B. Upper surface at fading: Near RHS Violet N88C. Under surface at first opening: Near RHS Violet N88B. Under surface at maturity: Near RHS Violet N88B. Under surface at fading: Near RHS Violet N88C.
Fragrance: No.
Involucral bracts:
*Arrangement*.—Rotate, spirally placed on involucrum.
*Number*.—Approximately 50.
*Length*.—Approximately 1.3 cm.
*Width*.—Approximately 0.5 cm.
*Shape*.—Elliptic.
*Apex*.—Narrow apiculate.
*Base*.—Cuneate.
*Margin*.—Sharp serrate to ciliate (not sharp to the touch).
*Texture*.—Smooth, very slightly glossy.
*Color*.—Inside color near RHS Green 137C. Outside color near RHS Green 137C.

Peduncles:

*Length*.—Average 9.3 cm.

*Width*.—Average 0.3 cm.

*Texture*.—Strong, dull, moderately pubescent, hair color near RHS Greyed-White 156D.

*Color*.—Near RHSGreen 138C.

Pedicels: No pedicels present, inflorescences directly on top of peduncles.

REPRODUCTIVE ORGANS

Androecium:

*Stamens per disc floret*.—5.

*Filament length*.—Approximately 0.4 cm.

*Filament color*.—Near RHS Violet N87D.

*Anther shape*.—Linear.

*Anther length*.—About 0.4 cm.

*Anther color*.—Near RHS White NN155D.

*Pollen amount*.—Low.

*Pollen color*.—Near RHS White NN155D.

Gynoecium:

*Pistil length*.—Approximately 1.5 cm.

*Stigma shape*.—Cleft.

*Stigma color*.—Near RHS White NN155D.

*Style length*.—About 1.2 cm.

*Style color*.—Near RHS White NN155D.

*Ovary color*.—Near RHS Green-White 157D.

OTHER CHARACTERISTICS

Seeds and fruits: Not observed to date.

Disease/pest resistance: Neither resistance nor susceptibility to normal diseases and pests of *Stokesia* has been observed.

Temperature tolerance: The new variety tolerates low temperatures to at least −5° C. and has been observed to tolerate high temperatures to at least 35° C. Plants can tolerate infrequent Summer watering.

What is claimed is:

1. A new and distinct cultivar of *Stokesia laevis* plant named 'MELS BLUE' as herein illustrated and described.

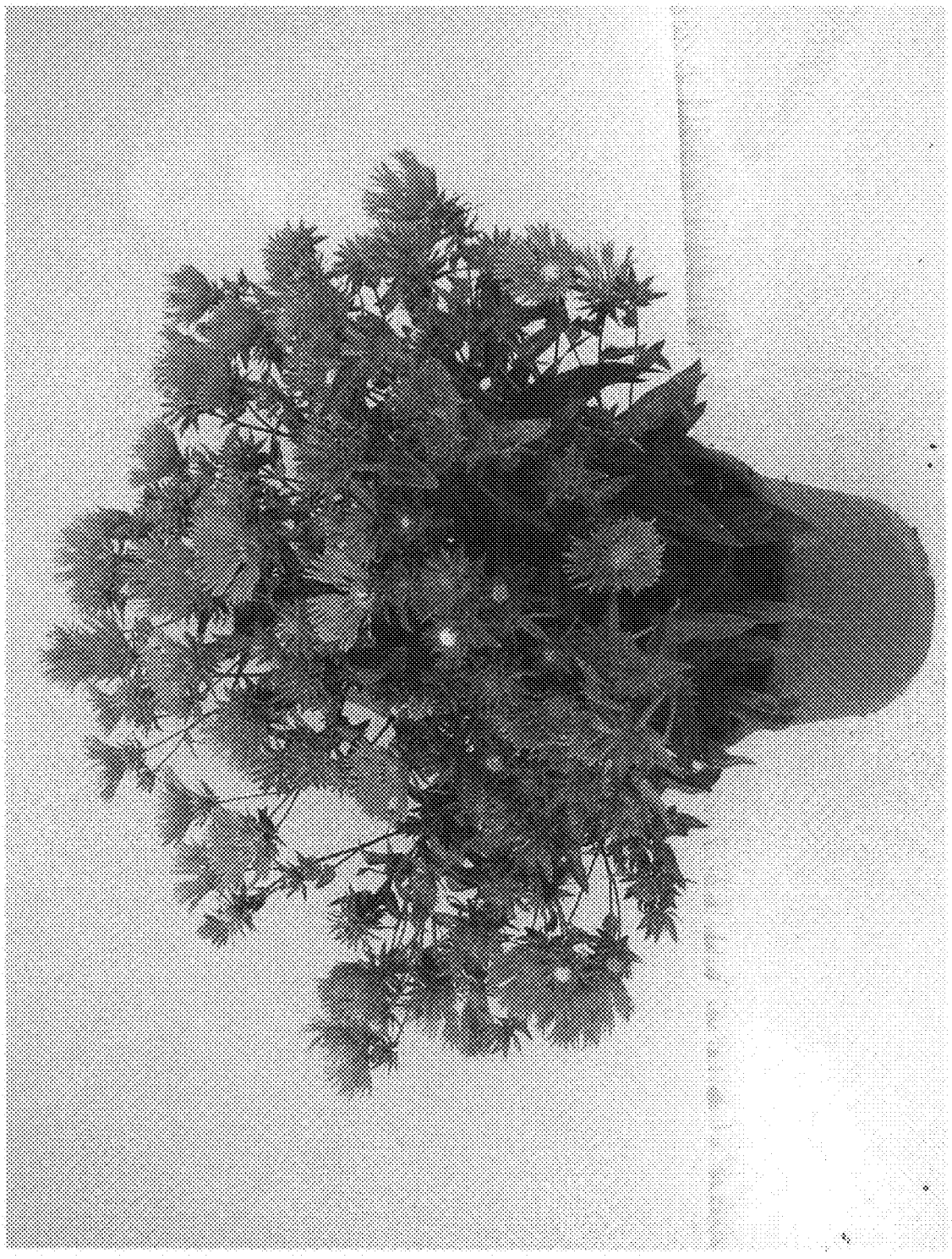

* * * * *